United States Patent [19]

Schwindeman

[11] Patent Number: 5,493,044

[45] Date of Patent: Feb. 20, 1996

[54] PROCESS FOR PREPARING ALKYLSILYL OR ARYLSILYL ETHERS

[75] Inventor: James A. Schwindeman, Shelby, N.C.

[73] Assignee: FMC Corporation, Philadelphia, Pa.

[21] Appl. No.: 326,681

[22] Filed: Oct. 20, 1994

[51] Int. Cl.⁶ ..................................................... C07F 7/18
[52] U.S. Cl. ............................................................. 556/471
[58] Field of Search .............................................. 556/471

[56] References Cited

U.S. PATENT DOCUMENTS

| | | | |
|---|---|---|---|
| 3,055,927 | 9/1962 | Pollock | 556/471 |
| 3,522,284 | 7/1970 | Kotzsch | 556/471 |
| 3,806,549 | 4/1974 | Foley | 556/471 |
| 4,060,538 | 11/1977 | Kotzsch et al. | 556/471 |
| 4,173,576 | 11/1979 | Seiler et al. | 556/471 |
| 4,851,558 | 7/1989 | Nishida et al. | 556/471 |
| 5,142,082 | 8/1992 | Sato et al. | 556/471 X |

OTHER PUBLICATIONS

E. J. Corey and A. Venkateswarlu, J. Amer. Chem. Soc., 6190–6191, (1972).
Protective Groups in Organic Synthesis, 2nd Ed., T. W. Green and P. G. M. Wuts, pp. 77–80, Aug. 1972.

*Primary Examiner*—Paul F. Shaver
*Attorney, Agent, or Firm*—Charles C. Fellows; Robert L. Andersen

[57] ABSTRACT

A process for preparing alkylsilyl and arylsilyl ethers of the formula $$(R-O-SiR^1R^2R^3)$$

wherein R, R1, R2 and R3 are independently selected from the group consisting of hydrogen, alkyl groups containing one to twenty carbon atoms, substituted alkyl groups containing one to twenty carbon atoms, aryl groups containing six to eighteen carbon atoms, substituted aryl groups containing six to eighteen carbon atoms, hetero aryl groups containing four to eighteen carbon atoms, and substituted hetero aryl groups containing four to eighteen carbon atoms, with the proviso that R is never hydrogen, by reacting, in a hydrocarbon solvent, a chlorosilane of the formula $R^1R^2R^3Si-Cl$ wherein $R^1$, $R^2$, and $R^3$ are independently selected from hydrogen, alkyl groups containing one to twenty carbon atoms, substituted alkyl groups containing one to twenty carbon atoms and aryl groups containing six to eighteen carbon atoms, substituted aryl groups containing six to eighteen carbon atoms, hetero aryl groups containing four to eighteen carbon atoms, and substituted hetero aryl groups containing four to eighteen carbon atoms with an alcohol of the formula ROH wherein R is an alkyl group containing one to twenty carbon atoms, a substituted alkyl group containing one to twenty carbon atoms, an aryl or substituted aryl group containing six to eighteen carbon atoms, or a hetero aryl or substituted hetero aryl group containing four to eighteen carbon atoms, in the presence of an organic acid acceptor (base) in a hydrocarbon solvent.

7 Claims, No Drawings

PROCESS FOR PREPARING ALKYLSILYL OR ARYLSILYL ETHERS

The present invention concerns a process for the preparation of alkylsilyl or arylsilyl ethers in high yield and excellent assay in hydrocarbon solution by the reaction of an alkyl alcohol or phenol with a chlorosilane.

Alcohol, amine and other functional groups are frequently masked during the course of a multi-step organic synthesis. Variously substituted silyl ethers (R—O—SiR$^1$R$^2$R$^3$) are a very common class of alcohol protecting group. The most commercially significant silicon based protecting group is the t-butyldimethylsilyl (R—O—SiMe$_2$t-Bu). These ethers are typically prepared by the reaction of the appropriate alcohol (R—OH) or phenol (ArOH) with a chlorosilane (R$^1$R$^2$R$^3$Si—Cl), in the presence of an acid scavenger, typically imidazole. The solvent is typically polar dimethylformamide (DMF) or tetrahydrofuran (THF), or environmentally unfriendly methylene chloride. An aqueous work-up followed by solvent extraction are necessary to separate the solvent and imidazole hydrochloride by-product from the desired alkylsilyl ether. Drying and concentration of the organic phase affords the desired alkylsilyl or arylsilyl ether. The ether can then be purified by chromatography, distillation, or recrystallization.

The literature methods for the preparation of these compounds are typically conducted in an expensive, polar dimethylformamide (DMF) or tetrahydrofuran (THF), or environmentally detrimental (methylene chloride) solvent. The original reference to the preparation of t-butyldimethylsilyl ethers (E. J. Corey and A. Venkateswarlu, J. Amer. Chem. Soc., 94, 6190 (1972)) employed dimethylformamide as the solvent and imidazole as the acid acceptor. Numerous variations of this procedure have appeared, particularly in the arena of solvent and acid acceptor/scavenger. In addition to DMF, the solvents most frequently employed are methylene chloride or THF. For a general summary of reaction conditions employed for the preparation of t-butyldimethylsilyl ethers, see Protecting Groups in Organic Synthesis, 2nd Ed., T. W. Greene and P. G. M. Wuts, pp. 77–80. Each of these procedures requires an aqueous work-up, to remove the imidazole hydrochloride by-product. The aqueous work-up adds significantly to the processing cost for this reaction. In addition, the solvents must be purified and dried before they can be recycled into the reaction. These procedures also typically employ an excess of the silylation agent and the acid scavenger. These excess reagents also contribute to the raw material cost of the reaction, and the excess must be removed from the desired product.

The present invention provides a process for preparing alkylsilyl or arylsilyl ethers in high yield and high purity by reacting a chlorosilane of the formula R$^1$R$^2$R$^3$SiCl wherein R$^1$, R$^2$ and R$^3$ are independently selected from hydrogen, alkyl and substituted alkyl groups containing one to twenty carbon atoms and aryl or substituted aryl groups containing five to eighteen carbon atoms with an alkyl alcohol of the formula ROH wherein R is an alkyl or substituted alkyl group containing one to twenty carbon atoms, a phenol or substituted phenol group containing six to eighteen carbon atoms, or a hetero aryl or substituted hetero aryl group containing four to eighteen carbon atoms in a hydrocarbon solvent, the alcohol is added last to the reaction mixture, and in the presence of an organic base, most preferably imidazole. The chlorosilane is used in amounts of 1.00 to 1.50 molar equivalents and the organic base in amounts of 1.00 to 1.50 molar equivalents per molar equivalent of alkyl alcohol or phenol at a temperature of 20° C. to 120° C.

This newly developed process eliminates the aqueous work-up inherent in the prior art processes. Mere filtration of the reaction mixture (to remove the imidazole hydrochloride) and solvent removal afforded the desired silyl ether in quantitative yield and excellent assay. The material could be further purified by distillation or recrystallization, if desired. Large excesses of the silyl chloride and imidazole starting materials are also avoided by this procedure. This makes the entire procedure more cost effective than the literature references.

Advantages of the invention are:

Environmentally objectionable and expensive solvents are avoided.

Only stoichiometric amounts of silyl chloride and imidazole are needed for good conversion to the alkylsilyl or arylsilyl ethers.

High yield and excellent assay of the silyl ethers are obtained.

The reaction work-up is very simple. The imidazole hydrochloride by-product is removed by simple filtration. An aqueous work-up is thus avoided. The imidazole hydrochloride filter cake is recovered in a form that is readily recycled.

The filtrate solution can be employed directly in subsequent reactions as is, or the solvent can be removed to afford the pure silyl ethers.

The solvent recovered from the stripping operation can be reused in subsequent silylation reactions, without further processing (such as drying).

It was unexpected that alkylsilyl and arylsilyl ethers could be prepared in hydrocarbon solution in high yield. Excellent conversion rates were obtained, despite the fact that the acid acceptor, imidazole, remained insoluble in the reaction medium throughout the reaction. Further, this discovery remarkably simplified the reaction work-up. The by-product imidazole hydrochloride was easily removed by filtration from the reaction medium. Concentration of the filtrate afforded the alkylsilyl or arylsilyl ether in high yields.

The new procedure for the preparation of the alkylsilyl or arylsilyl ether employed a reactor into which was charged the chlorosilane (R$^1$R$^2$R$^3$Si— Cl), a stoichiometric amount of imidazole, then the hydrocarbon solvent. The chlorosilane rapidly dissolved in the solvent. The imidazole remained insoluble. A stoichiometric amount of the alcohol or phenol was then added to this heterogeneous reaction mixture. An exotherm was detected during the addition. A very fine precipitate of imidazole hydrochloride rapidly developed. If a more rapid reaction was desired, the reaction mixture could be heated to 40°–50° C. The silyl ether remained in solution. The progress of the reaction was conveniently monitored by gas chromatography. The stirrer was halted, the solids settled to the bottom of the flask, and an aliquot of the supernatant solution was withdrawn and analyzed. When all the starting alcohol had been converted to silyl ether, the reaction mixture was allowed to cool to room temperature. The insoluble imidazole hydrochloride was removed by filtration of the reaction mixture by use of a pressure filter. The reactor was rinsed with additional hydrocarbon solvent. The muds were reslurried with further volumes of the hydrocarbon solvent. The filtrate samples were combined, then concentrated at reduced pressure on a rotary evaporator.

The crude alkylsilyl ether was isolated in excellent yield and assay from this process. A wide variety of primary and secondary alcohols, and diols were silylated under the reaction conditions. The alkylsilyl or arylsilyl ethers produced by this process could be further purified by distillation, chromatography, or recrystallization, if required. Clearly a wide variety of other differently substituted silyl ethers could be synthesized by this process.

Chlorosilanes useful in the practice of this invention include but are not limited to t-butyldimethylsilyl chloride, t-butylmethylsilyl chloride, methylphenylsilyl chloride, triisopropylsilyl chloride, dimethylphenylsilyl chloride, diphenylmethylsilyl chloride, t-butyldiphenylsilyl chloride, trimethylsilyl chloride, triethylsilyl chloride, triphenylsilyl chloride, diethylisopropylsilyl chloride, and the like.

Alkyl alcohols, substituted alkyl alcohols and diols useful in the practice of this invention include but are not limited to primary and secondary alcohols, and diols, such as 2-octanol, 1,6-hexanediol, 1-hexanol, 2-methyl-1-butanol, 6-chloro-1-hexanol, 1-octanol, 3-octanol, 4-octanol, 4-chloro-1-butanol, 3-chloro-1-propanol, 3-chloro-2,2-dimethyl-1-propanol, 2-butanol, cyclohexanol, cyclopentanol, ethylene glycol, propylene glycol, 1,5-pentanediol, 2,2-dimethyl-1,3-propanediol, 2-methyl-1,3-propanediol, 1,4-butanediol, 5-chloro-1-pentanol, 2-chloro-1-ethanol, 8-chloro-1-octanol, 3-methoxy-1-butanol, 2-methyl-1-pentanol, 2-ethyl-1-hexanol, benzyl alcohol, 4-methoxybenzyl alcohol, 2-(4-vinylphenyl)ethanol, 2-(3-vinylphenyl)ethanol, 2-(2-vinylphenyl)ethanol, 4-vinylbenzyl alcohol, 3-vinylbenzyl alcohol, 2-vinylbenzyl alcohol, furfuryl alcohol, tetrahydrofurfuryl alcohol, phenethyl alcohol, 2-propen-1-ol, and the like.

Phenols and substituted phenols useful in the practice of this invention include, but are not limited to phenol, 2-methylphenol, 3-methylphenol, 4-methylphenol, 2,4-dimethylphenol, 3,5-dimethylphenol, 2-chlorophenol, 3-chlorophenol, 4-chlorophenol, 2,4-dichlorophenol, 3,5-dichlorophenol, 2,4,6-trichlorophenol, 2-fluorophenol, 3-fluorophenol, 4-fluorophenol, 2,4-difluorophenol, 3,5-difluorophenol, 2,4,6-trifluorophenol, 2-chloro-4-fluorophenol, 2-fluoro-4-chlorophenol, 4-hydroxystyrene, 3-hydroxystyrene, 2-hydroxystyrene, 4-hydroxy-alpha-methylstyrene, 3-hydroxy-alpha-methylstyrene, 2-hydroxy-alpha-methylstyrene, 2-hydroxyacetophenone, 3-hydroxyacetophenone, 4-hydroxyacetophenone, methyl 4-hydroxybenzoate, ethyl 4-hydroxybenzoate, n-propyl 4-hydroxybenzoate, n-butyl 4-hydroxybenzoate, catechol, resorcinol, hydroquinone, 1-naphthol, 2-naphthol, and the like.

Organic bases useful in the practice of this invention as acid acceptors include but are not limited to imidazole, pyrrole, pyrazole, a triazole, a tetrazole, 2,4,6-collidine, 4-dimethylaminopyridine, 2,6-lutidine, 1,8-diazabicyclo[5.4.0]undec-7-ene, 1,5-diazabicyclo[4.3.0]non-5-ene, 1,4-diazabicyclo[2.2.2]octane, and the like. Mixtures of these organic bases can also be employed in this invention.

Solvents useful in the practice of this invention include but are not limited to pentane, hexane, heptane, octane, cyclopentane, cyclohexane, decalin, tetralin, benzene, toluene, ethylbenzene, xylene, cumene, cymene, durene, isodurene, and the like. Mixtures of these solvents can also be employed in this invention.

The preferred reaction conditions are: hydrocarbon solution; reactants in the proportions of 1.00 to 1.50 molar equivalents of the chlorosilane (most preferred 1.00 to 1.05 molar equivalents); 1.00 to 1.50 molar equivalents of acid acceptor (most preferred 1.00 to 1.10 molar equivalents); an organic base as the acid acceptor (most preferred imidazole); the molar equivalent of alcohol is added to the reaction mixture last; reaction temperatures vary from room temperature to the reflux temperature of the solvent, that is from about 20° to about 100° C., with the most preferred temperatures being from about 40° to about 50° C.; removal of the acid acceptor hydrochloride salt by filtration; and if desired, concentration of the filtrate to afford the desired alkylsilyl ether. The reaction is usually conducted at atmospheric pressure. Higher pressures can be used; but this adds to the expense of operation and equipment cost.

The general method of operating the process of this invention employs a reactor equipped with a reflux condenser, means for heating the reactor, optionally for cooling the reactor, a temperature indicating device, means for controlling the reaction temperature, ingress and egress means for inert gases, although the egress may be by way of the reflux condenser, an agitator, ingress and egress means for adding the reactants and removing the product and means for agitating the reaction mass. The reactor can be made of ordinary materials used in constructing chemical process equipment. Of course, glass lined and other chemical and/or corrosion resistant materials of construction can be used.

The following examples further illustrate the invention.

EXAMPLE 1

Preparation of 2-(t-Butyldimethylsilyloxy)-octane
Lot 8612, 461-95

A one liter, three-necked flask was equipped with a mechanical stirrer, a 250 ml. pressure-equalizing addition funnel, and a Claisen adapter fitted with a thermocouple connected to a THERM-O-WATCH®, a reflux condenser, and an argon inlet. This apparatus was dried in an oven overnight at 125° C., assembled hot, and allowed to cool to room temperature in a stream of argon. The flask was charged with 102.00 grams (0.677 mole, 1.01 equivalents) of t-butyldimethylsilyl chloride, 47.89 grams (0.704 mole, 1.05 equivalents) of imidazole, and 400 grams of cyclohexane. The t-butyldimethylsilyl chloride rapidly dissolved in the reaction medium. The resultant slurry was stirred at 375 RPM. 2-Octanol, 87.25 grams (0.67 mole, 1.00 equivalent) was added dropwise from the addition funnel. A modest exotherm was detected. Total feed time was 38 minutes. The progress of the reaction was monitored by gas chromatography (GC). An aliquot of the clear supernatant was injected into the GC. After one hour, the conversion was 76%. The reaction mixture was then heated to 40° C. with a heating mantle, controlled by a THERM-O-WATCH®. After stirring for 24 hours, the conversion was 99.2%. Further stirring for an additional 16 hours raised the conversion to 99.6%. The reaction mixture was allowed to cool to room temperature, then transferred to a glass pressure filter. The filtrate was collected in a dry, one liter flask. The filter cake was rinsed with additional cyclohexane (2×170 ml). The solvent was removed on the rotary evaporator, with the bath temperature set at 35° C.

This afforded a clear, colorless oil, yield=163.11 grams (99.7%).

Analysis of this material by GC indicated it was 96.9% assay product. addition, the stripped solution contained 1.1% cyclohexane, 0.04% t-butyldimethylsilyl chloride, 0.3% 2-octanol, and 1.7% unknowns.

EXAMPLE 2

Preparation of 1,6-Bis-(t-Butyldimethylsilyloxy)-hexane
Lot 8627, 451-3

A one liter, three-necked flask was fitted with a mechanical stirrer, and a Claisen adapter fitted with a thermocouple connected to a THERM-O-WATCH®, and an argon inlet. This apparatus was dried in an oven overnight at 125° C., assembled hot, and allowed to cool to room temperature in a stream of argon. The flask was charged with 154.50 grams (1.025 mole, 2.05 equivalents) of t-butyldimethylsilyl chloride, 71.48 grams (1.05 mole, 2.1 equivalents) of imidazole, and 200 grams of hexane. The t-butyldimethylsilyl chloride rapidly dissolved in the reaction medium. The resultant slurry was stirred at 375 RPM. 1,6-Hexanediol, 59.09 grams (0.50 mole, 1.00 equivalent), was then added to the reaction flask, followed by an additional 200 grams of hexane. No exotherm was detected. The 1,6-hexanediol remained insoluble in the reaction medium. After stirring at room temperature for one hour, the reaction mixture was heated to 40° C. with a heating mantle, controlled by a THERM-O-WATCH®. The reaction exothermed as the heat was applied. The heating mantle was removed, until the exotherm subsided. The maximum temperature observed was 55.8° C. A heavy precipitate formed, which did not stir. After a few minutes, these solids broke loose. The reaction mixture was then maintained at 40° C. with the heating mantle. The progress of the reaction was monitored by gas chromatography (GC). An aliquot of the clear supernatant was injected into the GC. After four hours, all the starting diol had been consumed. Both the mono-protected compound and the bis-protected compound were detected by GC. The ratio of bis: mono was 4:1. After five hours, the ratio of bis: mono was 10:1. The heating mantle was removed, and the reaction mixture was allowed to stir at room temperature over the weekend. The ratio of bis: mono was 95:5. The reaction mixture was transferred to a dry pressure filter. The filtrate was collected in a dry, one liter flask. The filter cake was rinsed with additional hexane (2×250 ml). The solvent was removed on the rotary evaporator, with the bath temperature set at 40° C.

This afforded a clear, colorless oil, yield=176.37 grams (101%).

Analysis of this material by GC indicated it was 98.3% assay product. In addition, the stripped solution contained 0.3% hexane, 0.04% t-butyldimethylsilyl chloride, 0.9% mono-protected material, and 0.5% unknowns.

NMR (CDCl$_3$) 3.58 (t, 4H), 1.77–1.13 (m, 8H), 0.88 (s, 18H), and 0.01 (s, 12H).

EXAMPLE 3

Preparation of 1-(Triisopropylsilyloxy)-hexane Lot 8887, 461-25

A 250 ml, three-necked flask was fitted with a large magnetic, egg-shaped stir bar, a small, pressure-equalizing addition funnel, a thermocouple connected to a THERM-O-WATCH®, a reflux condenser, and an argon inlet. This apparatus was dried in an oven overnight at 125° C., assembled hot, and allowed to cool to room temperature in a stream of argon. The flask was charged with 32.46 grams (0.168 mole, 1.01 equivalents) of triisopropylsilyl chloride, 11.69 grams (0.172 mole, 1.03 equivalents) of imidazole, and 100 mls of hexane. 1-Hexanol, 17.03 grams (0.167 mole, 1.00 equivalent), was then added dropwise to the resultant slurry. A very mild exotherm was detected. The total feed time was five minutes. A heavy, white precipitate formed after a few more minutes stirring. The reaction mixture became very hard to stir. Therefore, an additional 25 mls of hexane was added to the reaction. The progress of the reaction was monitored by gas chromatography (GC). An aliquot of the clear supernatant was injected into the GC. The sample at 2.33 hours indicated the conversion to the desired product was 73.0%. The reaction mixture was heated to 40° C. with a heating mantle, controlled by the THERM-O-WATCH®. After stirring overnight at 40° C., the conversion had increased to 87.2%. The temperature was increased to 60° C. After seven hours at 60° C., the conversion was 90.0%. The reaction mixture was heated to reflux overnight, under a blanket of argon. The temperature was decreased to 60° C., and the reaction was analyzed by GC. The conversion was 95.2%. The reaction mixture was held at 60° C. for an additional seven hours, then the reaction mixture was allowed to stir at room temperature over the weekend. The conversion had reached 98.1%. The reaction mixture was transferred to a small, dry, Chemglass pressure filter. The tiltrate was collected in a dry, 500 ml flask. The filter cake was rinsed with additional hexane (2×100 ml). The solvent was removed on the rotary evaporator, with the bath temperature set at 40° C.

This afforded a clear, colorless oil, yield=43.23 grams (100%).

Analysis of this material by GC indicated it was 96.3% assay product. In addition, the stripped solution contained 0.5% hexane, 2.2% triisopropylsilyl chloride, 0.2% starting material, and 0.8% unknowns.

NMR (CDCl$_3$) 3.59 (t, J=6 Hz, 2H), and 1.75 0.45 (m, 32H).

EXAMPLE 4

Preparation of 1-(Dimethylphenylsilyloxy)-2-methylbutane Lot 8964, 461-57

A 250 ml, three-necked flask was fitted with a large magnetic, egg-shaped stir bar, a small, pressure-equalizing addition funnel, a thermocouple connected to a THERM-O-WATCH®, a reflux condenser, and an argon inlet. This apparatus was dried in an oven overnight at 125° C., assembled hot, and allowed to cool to room temperature in a stream of argon. The flask was charged with 28.74 grams (0.168 mole, 1.01 equivalents) of dimethylphenylsilyl chloride, 11.69 grams (0.172 mole, 1.03 equivalents) of imidazole, and 100 mls of hexane. 2-Methyl-1-butanol, 14.69 grams (0.167 mole, 1.00 equivalent), was then added dropwise to the resultant slurry. A very mild exotherm was detected. The total feed time was twelve minutes. A fine white precipitate formed almost immediately. The reaction mixture was heated to 40° C. with a heating mantle, controlled by the THERM-O-WATCH®. A more vigorous exotherm was noted as the heat was applied. The heating mantle was removed. After the exotherm had subsided, the reaction mixture was again heated to 40° C. with the heating mantle. The reaction mixture was stirred overnight at 40° C. The progress of the reaction was monitored by gas chromatography (GC). An aliquot of the clear supernatant was injected into the GC. The sample at 15 hours indicated all the starting material had been consumed, with the formation of a single, higher boiling component. The reaction mixture was allowed to cool to room temperature, then it was transferred to a small, dry, Chemglass pressure filter. The filtrate was collected in a dry, 500 ml flask. The filter cake was rinsed with additional hexane (2×100 ml). The solvent was removed on the rotary evaporator, with the bath temperature set at 40° C.

This afforded a clear, colorless oil, yield=37.19 grams (100%).

Analysis of this material by GC indicated it was 97.8% assay product.

NMR (CDCl₃) 7.59–7.04 (m, 5H), 3.23 (d, J=6 Hz, 2H), 1.75–0.39 (m, 9H), and 0.16 (s, 6H).

EXAMPLE 5

Preparation of
1-(t-Butyldiphenylsilyloxy)-2-methylbutane Lot 8982, 461-66

A 250 ml, three-necked flask was fitted with a large magnetic, egg-shaped stir bar, a small pressure-equalizing addition funnel, a thermocouple connected to a THERM-O-WATCH®, a reflux condenser, and an argon inlet. This apparatus was dried in an oven overnight at 125° C., assembled hot, and allowed to cool to room temperature in a stream of argon. The flask was charged with 46.27 grams (0.168 mole, 1.01 equivalents) of t-butyldiphenylsilyl chloride, 11.69 grams (0.172 mole, 1.03 equivalents) of imidazole, and 100 mls of hexane. 2-Methyl-1-butanol, 14.69 grams (0.167 mole, 1.00 equivalent), was then added dropwise to the resultant slurry. A very mild exotherm was detected. The total feed time was twelve minutes. A fine white precipitate formed almost immediately. The reaction mixture was stirred at room temperature, and monitored by GC analysis. An aliquot of the clear supernatant was injected into the GC. After seven hours, both starting materials were still present. Therefore, the reaction mixture was heated to 60° C. with a heating mantle, controlled by the THERM-O-WATCH®. The reaction mixture was stirred overnight at 60° C. The sample after 23.5 hours indicated all the starting material had been consumed, with the formation of a single, higher boiling component. The reaction mixture was allowed to cool to room temperature, then it was transferred to a small, dry, Chemglass pressure filter. The filtrate was collected in a dry, 500 ml flask. The filter cake was rinsed with additional hexane (2×100 ml). The solvent was removed on the rotary evaporator, with the bath temperature set at 40° C.

This afforded a clear, colorless oil, yield=55.12 grams (101.1%).

Analysis of this material by GC indicated it was 96.6% assay product.

NMR (CDCl₃) 7.97–7.612 (m, 4H), 7.61–7.28 (m, 6H), 3.56 (d, J=6 Hz, 2H), 1.81–0.60 (m, 9H), and 1.10 (s, 9H).

EXAMPLE 6

Preparation of
6-(t-Butyldimethylsilyloxy)-1-chlorohexane Lot 8296, 434-72

A 250 ml, three-necked flask was fitted with a large magnetic, egg-shaped stir bar, a thermocouple, reflux condenser, and an argon inlet. This apparatus was dried in an oven overnight at 125° C., assembled hot, and allowed to cool to room temperature in a stream of argon. The flask was charged with 15.09 grams (0.100 mole, 1.00 equivalents) of t-butyldimethylsilyl chloride, and 100 grams of cyclohexane. The silyl chloride rapidly dissolved, endothermically. 6-Chloro-1-hexanol, 13.96 grams (0.100 mole, 1.00 equivalent) was then weighed into the flask. After stirring at room temperature for fifteen minutes, the reaction mixture appeared hazy. The stirrer was halted, and a second, immiscible layer was observed in the bottom of the flask. Imidazole, 6.81 grams (0.100 mole, 1.00 equivalent) was then added to the reaction mixture. A fine white precipitate rapidly developed. The reaction mixture was stirred at room temperature, and monitored by GC analysis. An aliquot of the clear supernatant was injected into the GC. After five hours, both starting materials were still present, and the conversion to the desired product was 82.2%. The reaction mixture was stirred overnight at room temperature, under a blanket of argon. The sample after 30 hours indicated all the starting material had been consumed, with the formation of a single, higher boiling component. The reaction mixture was transferred to a small, dry, Chemglass pressure filter. The filtrate was collected in a dry, 500 ml flask. The filter cake was rinsed with additional cyclohexane (2×100 ml). The solvent was removed on the rotary evaporator, with the bath temperature set at 40° C.

This afforded a clear, colorless oil, yield=25.44 grams (101.5%).

Analysis of this material by GC indicated it was 98.3% assay product. In In addition, the stripped solution contained 0.5% cyclohexane, 0.2% t-butyldimethylsilyl chloride, and 1.0% unknowns.

Comparative Example

Preparation of
6-(t-Butyldimethylsilyloxy)-1-chlorohexane Lot 8353, 434-91

A 250 ml, three-necked flask was fitted with a large magnetic, egg-shaped stir bar, a thermocouple, a small, pressure-equalizing addition funnel, a reflux condenser, and an argon inlet. This apparatus was dried in an oven overnight at 125° C., assembled hot, and allowed to cool to room temperature in a stream of argon. The flask was charged with 16.20 grams (0.108 mole, 1.00 equivalents) of t-butyldimethylsilyl chloride, and 100 grams of cyclohexane. The silyl chloride rapidly dissolved, endothermically. 6-Chloro-1-hexanol, 15.06 grams (0.108 mole, 1.00 equivalent) was then added dropwise in five minutes. Triethylamine, 10.93 grams (0.108 mole, 1.00 equivalent) was then added dropwise to the reaction mixture. An exotherm was noted, and fumes of triethylamine hydrochloride were observed. A fine, white precipitate rapidly developed. The reaction mixture was stirred at room temperature, and monitored by GC analysis. An aliquot of the clear supernatant was injected into the GC. After one and a half hours, both starting materials were still present, and the conversion to the desired product was only 27.8%. The reaction mixture was stirred overnight at room temperature, under a blanket of argon. The sample after 21 hours indicated only a 53.3% conversion to the desired product. After 161.5 hours stirring, the conversion was still only 88.0%.

This example clearly indicates the inferiority of triethylamine as an acid scavenger in the silylation reaction.

What is claimed is:

1. A process for preparing alkylsilyl and arylsilyl ethers of the formula

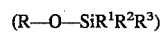

wherein R, R1, R2 and R3 are independently selected from the group consisting of hydrogen, alkyl groups containing one to twenty carbon atoms, substituted alkyl groups containing one to twenty carbon atoms, aryl groups containing six to eighteen carbon atoms, substituted aryl groups containing six to eighteen carbon atoms, hetero aryl groups containing four to eighteen carbon atoms, and substituted hetero aryl groups containing four to eighteen carbon atoms, with the proviso that R is never hydrogen, by reacting, in a hydrocarbon solvent, a chlorosilane of the formula $R^1R^2R^3Si-Cl$ wherein $R^1$, $R^2$, and $R^3$ are independently selected from hydrogen, alkyl groups containing one to twenty carbon atoms, substituted alkyl groups containing one to twenty carbon atoms and aryl groups containing six to eighteen carbon atoms, substituted aryl groups containing six to eighteen carbon atoms, hetero aryl groups containing four to eighteen carbon atoms, and substituted hetero aryl groups containing four to eighteen carbon atoms with an alcohol of the formula ROH wherein R is an alkyl group containing one to twenty carbon atoms, a substituted alkyl group containing one to twenty carbon atoms, an aryl or substituted aryl group containing six to eighteen carbon atoms, or a hetero aryl or substituted hetero aryl group containing four to eighteen carbon atoms, in the presence of an organic acid acceptor (base) selected from the group consisting of imidazole, pyrrole, pyrazole, a triazole, a tetrazole, 2,4,6-collidine, 4-dimethylaminopyridine, 2,6-lutidine, 1,8-diazabicyclo[5.4.0]undec-7-ene, 1,5-diazabicyclo[4.3.0]non-5-ene, 1,4-diazabicyclo[2.2.2]octane, and mixtures of these organic bases in a hydrocarbon solvent.

2. The process of claim 1 wherein the chlorosilane is t-butyldimethylsilyl chloride, t-butylmethylsilyl chloride, methylphenylsilyl chloride, triisopropylsilyl chloride, dimethylphenylsilyl chloride, diphenylmethylsilyl chloride, t-butyldiphenylsilyl chloride, trimethylsilyl chloride, triethylsilyl chloride, triphenylsilyl chloride, and diethylisopropylsilyl chloride.

3. The process of claim 1 wherein the alcohol is selected from 2-octanol, 1,6-hexanediol, 1-hexanol, 2-methyl-1-butanol, 6-chloro-1-hexanol, 1-octanol, 3-octanol, 4-octanol, 4-chloro-1-butanol, 3-chloro-1-propanol, 3-chloro-2,2-dimethyl-1-propanol, 2-butanol, cyclohexanol, cyclopentanol, ethylene glycol, propylene glycol, 1,5-pentanediol, 2,2-dimethyl-1,3-propanediol, 2-methyl-1,3-propanediol, 1,4-butanediol, 5-chloro-1-pentanol, 2-chloro-1-ethanol, 8-chloro-1-octanol, 3-methoxy-1-butanol, 2-methyl-1-pentanol, and 2-ethyl-1-hexanol, benzyl alcohol, 4-methoxybenzyl alcohol, 2-(4-vinylphenyl)ethanol, 2-(3-vinylphenyl)ethanol, 2-(2-vinylphenyl)ethanol, 4-vinylbenzyl alcohol, 3-vinylbenzyl alcohol, 2-vinylbenzyl alcohol, furfuryl alcohol, tetrahydrofurfuryl alcohol, phenethyl alcohol, 2-propen-1-ol.

4. The process of claim 1 wherein the phenol is selected from phenol, 2-methylphenol, 3-methylphenol, 4-methylphenol, 2,4-dimethylphenol, 3,5-dimethylphenol, 2-chlorophenol, 3-chlorophenol, 4-chlorophenol, 2,4-dichlorophenol, 3,5-dichlorophenol, 2,4,6-trichlorophenol, 2-fluorophenol, 3-fluorophenol, 4-fluorophenol, 2,4-difluorophenol, 3,5-difluorophenol, 2,4,6-trifluorophenol, 2-chloro-4-fluorophenol, 2-fluoro-4-chlorophenol, 4-hydroxystyrene, 3-hydroxystyrene, 2-hydroxystyrene, 4-hydroxy-alpha-methylstyrene, 3-hydroxy-alpha-methylstyrene, 2-hydroxy-alpha-methylstyrene, 2-hydroxyacetophenone, 3-hydroxyacetophenone, 4-hydroxyacetophenone, methyl 4-hydroxybenzoate, ethyl 4-hydroxybenzoate, n-propyl 4-hydroxybenzoate, n-butyl 4-hydroxybenzoate, catechol, resorcinol, hydroquinone, 1-naphthol, and 2-naphthol.

5. The process of claim 1 wherein the hydrocarbon solvent is selected from pentane, hexane, heptane, octane, cyclopentane, cyclohexane, decalin, tetralin, benzene, toluene, ethylbenzene, xylene, cumene, cymene, durene, isodurene, and mixtures thereof.

6. The process of claim 1 wherein the temperature of the reaction is between 20° C. and 120° C.

7. The process of claim 1 wherein the chlorosilane is used in amounts of 1.00 to 1.50 molar equivalents, and the organic acid acceptor in amounts of 1.00 to 1.50 molar equivalents for each molar equivalent of alkyl alcohol, substituted alkyl alcohol, phenol, or substituted phenol.

\* \* \* \* \*